United States Patent [19]
Gladney et al.

[11] Patent Number: 5,236,954
[45] Date of Patent: Aug. 17, 1993

[54] PARASITICIDAL COMPOSITION AND METHODS FOR ITS MAKING AND USE

[75] Inventors: Julie G. Gladney, McKinney, Tex.; David S. Seymour, Kansas City; Jack I. Shugart, Gurnee, Ill.; Robert G. Pennington, Rayville, Mo.

[73] Assignee: Pitman-Moore, Inc., Mundelein, Ill.

[21] Appl. No.: 707,629

[22] Filed: May 30, 1991

Related U.S. Application Data

[63] Continuation-in-part of Ser. No. 487,913, Mar. 5, 1990, abandoned.

[51] Int. Cl.⁵ .................. A61K 31/215; A61K 31/275
[52] U.S. Cl. ...................................... 514/531; 514/521
[58] Field of Search ................................ 514/521, 531

[56] References Cited

U.S. PATENT DOCUMENTS

| | | | |
|---|---|---|---|
| 2,074,188 | 3/1937 | Rippert | 514/72 |
| 4,404,223 | 9/1983 | Matthewson | 424/305 |
| 4,595,579 | 6/1986 | Broadbent | 514/65 |
| 4,607,050 | 8/1986 | Kieran et al. | 514/531 |
| 4,731,378 | 3/1988 | Naik et al. | 514/331 |
| 4,904,464 | 2/1991 | Albanese | 514/65 |

FOREIGN PATENT DOCUMENTS

| | | |
|---|---|---|
| 0045424 | 2/1982 | European Pat. Off. . |
| 0061208 | 9/1982 | European Pat. Off. . |
| 2436028 | 2/1976 | Fed. Rep. of Germany ........ 514/72 |
| 2002635 | 2/1979 | United Kingdom . |
| 2088212 | 6/1982 | United Kingdom ................. 514/65 |

*Primary Examiner*—Allen J. Robinson
*Attorney, Agent, or Firm*—Wendell Ray Guffey; Penny R. Slicer

[57] ABSTRACT

A liquid phase composition of a pyrethroid in concentrations greater than 50% w/w that may be used as a basis for other pyrethroid containing formulations in physical phases other than the liquid phase is described. A method of treatment utilizing the composition on domestic mammal is also described. The composition can be applied as a small dose to a localized region of the animal's body which is then delivered to relatively all of the animal's body surface by migration of the pyrethroid.

28 Claims, No Drawings

PARASITICIDAL COMPOSITION AND METHODS FOR ITS MAKING AND USE

This is a continuation-in part of U.S. patent application Ser. No. 07/487,913, filed on Mar. 5, 1990 and now abandoned which is incorporated herein by reference.

BACKGROUND OF THE INVENTION

This invention relates in general to a composition for controlling ectoparasites. More particularly this invention relates to such a composition employing a pyrethroid in concentrations greater than 50% by weight of the total composition.

Ectoparasidic arthropods such as ticks, flies and fleas are often found on mammals, such as humans and a variety of animals. Ectoparasites will feed off their mammal host and are a constant source of irritation to the host. It is therefore desirable to control such infestations. By control, it is meant that, desirably, about 80% by weight of all parasites on the host are killed or repelled. Control of tick infestation on all mammals, especially household pets, has recently assumed greater importance than at an other recent time because of the discovery that certain tick species may carry the microorganism responsible for the transmission of Lyme disease to humans.

While there are known compositions and methods for controlling ectoparasites, many of them are systemic products. That is, they are products containing active parasiticides that enter the bloodstream of the host in order to create the insecticidal effect. Systemic insecticides are generally less desirable if suitable alternatives exist. Because systemic products, even if topically applied, must enter into the host bloodstream, they are more likely to be toxic to the host. In addition, systemic products that are not applied topically can be difficult to administer. They may require injection equipment or involve the difficult task of getting an animal to swallow oral formulations.

Liquid compositions containing up to 50% by weight of a pyrethroid are known as are methods for applying said formulations topically. See for example, U.K. Pat. 2,088,212 to Kieran & Townsend. However, known compositions do not encompass the formulation of liquid compositions containing pyrethroid in an amount greater than 50% by weight of the total composition, like those of the instant invention. It is surprising that such concentrated formulations do not cause irritation and toxicity. It would be anticipated that highly concentrated solutions of a pyrethroid, when applied to the skin, would be absorbed into the host and result in systemic toxicity, or would cause severe skin irritation. The present invention encompasses a topical formulation of greater than 50% by weight of a pyrethroid that is non-irritating and non-toxic to the host animal. The present invention also encompasses a method of controlling ectoparasites wherein the total formulation can be applied as a small dose to one or more localized regions on the skin of the hosts. The concentrated formulation applied in this manner spreads over relatively all of the body surface of the host and effectively controls ectoparasites.

Although applicant does not wish to be bound by theory or speculation, it is believed that one reason why the prior art does not teach the use of such highly concentrated pyrethroid formulations is because of the solvent systems heretofore employed. For example, U.K. Patent No. 2,088,212 teaches the dissolution of solid pyrethroids into liquid formulations by using undesirable, irritating, organic solvents such as xylene, toluene, and cyclohexanone. It teaches the use of one of these solvents in conjunction with alkyl glycol ethers. It also teaches the use of combinations of the three organic solvents in conjunction with a glycol. The referenced U.K. patent does not teach the use of glycols without adding other undesirable and irritating components. Those skilled in the art would not expect that the weak solvent power of the glycols could be compatible with commercial production methods. When the active ingredients according to the present invention are formulated in an alkyl glycol ether solvent, the resulting liquid formulation can then be used as an ingredient in formulating other topical compositions.

Concentrations of more than 50% by weight make topical application of the composition more convenient and more aesthetic than ever before. The higher the concentration, the smaller the dose for effective ectoparasite control. A small dose can be applied to a relatively small region of the skin, thus preventing the host from being covered with solvent. This formula and method of application is particularly useful for treating domestic animals, because the animal will not drip solvent or feel sticky when petting immediately after application. Such small doses can be applied without the treated animal being made aware thus easing administration. Although the composition is applied as one or more small doses to a localized region on the animal, the pyrethroid translocates to effectively control ectoparasite infestation over relatively all of the animal. Formulations containing more than 50% by weight of a pyrethroid thus obtain many advantages not taught by the prior art of using formulations with maximum concentrations of up to 50% by weight of the total formulation.

Topical compositions can be formulated to take a variety of physical states. They can be a mixture of liquids or a solid active agent can be dissolved in solution. Alternatively, the active agent may be carried in a suspension or emulsion, or may be as a microencapsulation and carried in a suspension. The suspensions can be water or oil based sols, gels, or ointments. Emulsion carriers contain both aqueous and oily components and can take the form of creams, lotions, or ointments. or ointments.

In addition, topical administration is further made convenient if the active agent insecticide is contained in an optimal composition. An optimal composition has the following characteristics. The active agent comprises more than 50% by weight of the formulation so that the smallest effective dose may be achieved. Although the mechanism is not fully known, it is thought that during application and while on the host, either or both the carrier components and the active agent of the formulation facilitates distribution of the agent over the surface of the animal and to the parasite. The carrier may also facilitate migration of the pyrethroid component to cover relatively all of the animal body surface for effective ectoparasite control. In the optimal composition, the carrier may also comprise ingredients that soothe or prevent irritation as well as merely employing solvents that are non-irritating.

The choice of carrier can also be varied to optimize frequency of dosing according to particular environmental conditions. For example, oily carriers resist washing. Formulations comprised of oily carriers reduce dosing frequency for hosts exposed to rain and water. Formulations comprised of aqueous carriers are more suited to dry environs. If the host is in dry environs the aqueous formulation is less likely to be washed off and the required frequency of dosing remains low.

Formulations with pyrethroid concentrations in excess of 50% by weight can be packaged in a single dose package. For example, a single 1 cubic centimeter (cc) dose of a liquid formulation comprised of permethrin and 35% 2-(2-methoxy-ethoxy)ethanol can be packaged in a collapsible 1 cc tube. Because, the formulation avoids the use of strong organic solvents like xylene, cyclohexanone, and toluene, there is greater choice of tube material. Single dose containers make storage and disposal more convenient for animal owners.

Multiple dose liquid formulations can be packaged in containers, possibly photoresistant containers, of more than 1 cc capacity. The high concentration composition also decreases container size requirements for multiple dose containers as well as the container size requirements for single dose containers for larger animals. Again, the smaller container sizes are more conveniently stored and disposed.

SUMMARY OF THE INVENTION

It has been discovered that a composition including a pyrethroid in concentrations greater than 50% and up to 95% by weight of the total composition can be prepared and that said highly concentrated composition is effective for topical application for control of ectoparasites such as fleas, flies, and ticks on some mammals, while remaining non-toxic and non-irritating to the host.

In one aspect of the invention the pyrethroid used is permethrin. The composition preferably comprises 65% by weight permethrin in a carrier, preferably the solvent carrier 2-(2-methoxyethoxy)ethanol. The composition may include other inert ingredients such as perfumes, skin conditioners or coat sheeners. A preferred composition is in a pourable form so that it can be easily applied to the fur or skin of host animals. The preferred composition is non-irritating to the host skin, coat, and fur and is also not systemically toxic to the host.

Another aspect of this invention encompasses a method for administering an effective amount of pyrethroid to control ectoparasite infestation over the entire body surface of the host. A composition comprising a pyrethroid, preferably permethrin, in an amount ranging from above 50% and up to 95% by weight is applied as one or more small doses to one or more localized regions on the host. Although the exact mechanism is not known, it is thought that the pyrethroid component translocates by migration to cover relatively all of the mammal's body surface within a short period of time. The concentrated dose thus effectively controls ectoparasite infestation over the entire body surface of the host.

DETAILED DESCRIPTION OF THE INVENTION

The present invention is a composition for controlling ectoparasites that can be found on mammals and to methods for preparing and using the composition. Generally, the composition comprises pyrethroid and a carrier.

Pyrethroids are a class of chemicals, that have shown efficacy against ectoparasites. Suitable pyrethroids include permethrin, phenothrin, cypermethrin, cyhalothrin, lambda cyhalothrin, cyfluthrin, cyphenothrin, tralomethrin, tralocythrin, deltamethrin, sluvalinate fluvinate, flumethrin and fenvalerate. The most preferred pyrethroid for use in this invention is permethrin. Permethrin has a technical name of 3-(phen-oxyphenyl)-methyl-(1RS)-cis,trans-3-2,2-dichloroethenyl)-2,2-dimethylcyclopropane carboxylate and a formula of:

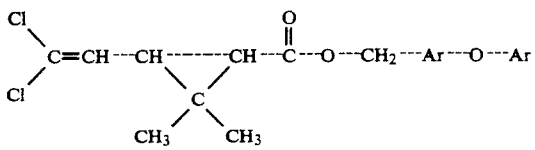

[Ar denotes a phenyl group]

Permethrin has a molecular weight of 391.29 grams/mole and technical permethrin comprises from about 25 to 80% cis and about 20–75% trans isomers by weight. In the insecticidal composition of the invention, technical permethrin is suitable and it preferably has a minimum amount of the tran isomer of about 45% by weight and a minimum amount of cis isomer of about 35% by weight.

In the formulation of an ectoparasiticide composition according to the instant invention the concentration of permethrin is from above 50% up to about 95% (by weight) with a preferred range of 60–70% (by weight) and a most preferred range of 65–70% (by weight). The remaining portion of the composition is a carrier substance.

Any carrier that can deliver a pyrethroid, preferably permethrin, is a suitable carrier substance to comprise the pyrethroid composition so long as the carrier is also not irritating to the host's skin and not systemically toxic to the host and allows distribution to and contact with or absorption by the target parasite. Some suitable liquid carriers include most alcohols, aromatic petroleum products, corn oil, eucalyptus oil, dimethyl glycol, glycol ether, and 2-(2-methoxybutoxy)ethanol and 2-(2-methoxyethoxy)ethanol. The compound 2-(2-methoxyethoxy)ethanol is the preferred liquid carrier for use in the insecticidal composition of the present invention.

It is surprising to find that the insecticidal composition of the present invention comprising such a high percentage of the active ingredient, a pyrethroid, is effective against ectoparasites while remaining non-irritating and non-toxic to the host. A composition of the insecticidal composition having such a high concentration of active ingredient also allows for small, easily applied, and yet effective doses. A particularly effective method of application consist of applying the composition to one or more localized regions of the host, such as by applying a small spot of the composition on an animal at the region between its shoulder blades. It is believed that the pyrethroid component translocates within a relatively short period of time to effectively cover the entire surface of the host's body. No special expertise is required to apply the treatment so animal owners may do so without the assistance of a health care professional and without special equipment.

Other inert ingredients can be added to the present composition and can include spreading agent, synergists, attractants, repellents, adhesion promoters, surface active agents, stabilizers, skin conditioners, perfumes, coat sheeners and coloring agents. Additional agents such as insecticides and growth regulators can also be included in the composition of the present invention.

Suitable spreading agents are liquids which distribute themselves particularly readily on the skin. Diproylene glycol monomethylether is a particularly suitable spreading agent for inclusion within the compositions of the present invention. Isopropyl myristate is within the compositions of the present invention. Isopropyl myristate is another commonly used spreading agent. The desirable properties of spreading agents, sometimes referred to as spreading oils, are generally well known to those skilled in the art. Attractants include phermones such as 2,6-dichlorophenol. Repellents include citronellol, diethyl toluimide, dimentyl phthalate, and the like.

Of the other inert ingredients that can be utilized with the present invention there are the adhesion promoters. Adhesion promoters include carboxymethyl-cellulose, methylcellulose and other cellulose derivatives and starch derivatives, polyacrylates, aglinates gelatin, gum arabic, polyvinylpyrrolidone, polyvinyl alcohol, co-polymers of methyl vinyl ether and maleic anhydride, polyethylene glycols, paraffins, oils, waxes and hydrogenated castor oil, colloidal silicic acid or mixtures of the substances mentioned.

The compositions of the present invention do not normally contain surface active agents; however these may be included if desired. Surface-active agents (comprising emulsifiers and wetting agents) include:

1. anionic surface active agents, such as Sodium lauryl sulfate, fatty alcohol ether-sulfates and monoethanolamine salts of mono-/di-alkylpolygylcol ether orthophosphoric acid esters, 2. cationic surface active agents, such as cetyltrimethyl-ammonium chloride, 3. amphophilic surface-active agents, such as Di-sodium-N-lauryl-amino-diproprionate or lecithin, and 4. non-ionic surface active agents, for example, polyoxyethylated castor oil, polyoxyethylated sorbitane monoleate, sorbitan monostearate, ethyl alcohol, glycerol monostearate, polyoxyethylene stearate and alkylphenol polyglycol ethers.

For preventing chemical degradation which occurs in the case of some active compounds, stabilizers may also be used and include, for example, antioxidants, such as tocopherols, butyl-hydroxyanisole, butylhydroxtoluene and carbodiimides, e.g. 2,2-6,6-tetraisopropyldiphenylcarbo-diimide) and scavengers such as epichlorhydrin. Coloring agents include conventional dyes which are soluble in the carrier of the present invention, such as Sudan red or Oil Golden Yellow.

In order to prepare the insecticidal composition of the present invention, a pyrethroid is heated to 65-80 degrees Centrigrade until any crystals present are liquefied. The liquid is then mixed until uniform. A liquid carrier solvent is placed into a separate unheated vessel. The permethrin is then added to the vessel. The permethrin and carrier solvent are then mixed to uniformity. Additives may also be included in the vessel and mixed into the formulation. The additives comprise additional pharmaceutical additives like skin conditioners, perfumes, coat sheeners, and spreading agents.

In the preferred embodiment of this invention, permethrin is heated to about 65 degrees Centrigrade. The carrier 2-(2-methoxyethoxy)ethanol is placed in a clean take and the permethrin added and mixed until uniform. After the permethrin has been formulated into this simple liquid mixture, the mixture may serve as a starting point for the formulation of topical preparations in other physical states. For instance, gelling agents may be added to create topical preparations in the form of gels and sols. Gases may be added to create topical preparations that can be delivered as aerosols. Other formulating agents may be added to the liquid mixture to create ointments and pastes.

The insecticidal composition of the present invention is suitable for use on most mammals including humans, horses, cattle, giraffes and domesticated companion animals such as dogs. Because it is so surprisingly non-toxic, it may be used on pups as well as adult mammals. It is also effective against a variety of parasites including ticks, fleas, flies, keds, and mites.

The composition according to the present invention is particularly useful for horses and other large mammals because the doses required are much smaller as compared to the pyrethroid compositions of 50% by weight or lesser concentrations taught by the prior art. The insecticidal composition of this invention is useful for the control of arthropods, insects and ascarine ecto-parasites such as fleas, ticks, flies, keds, and mites. Its most preferred use is for the control of ticks and fleas on dogs.

The composition ma be applied to the host animal by any conventional method for the localized application of compositions, for example by dropping a small volume of liquid composition on the mammal's body. One advantage of the use of a highly concentrated composition is that only a small volume is necessary. The composition applied in this manner appears to exhibit migration, wherein the pyrethroid component is translocated to other regions on the animal body. This migration or spreading effect enables administration of the pyrethroid to relatively all of the animal body surface for ectoparasitic control.

Since the composition has a high concentration of pyrethroid, this small application of a spot or line on the animal will effectively control insect and aracnid parasite infestations on mammals from within three to twenty four hours post administration and for u to four weeks post administration. This method is non-toxic and the concentrated composition does not irritate the animals skin. While a necessary amount of the composition of the present invention needed to be applied for effective insecticidal activity depends upon the size of the animal and the precise concentration and delivery capabilities of the particular composition, a 1 cubic centimeters (cc) volume of the preferred liquid composition has been found to be effective on dogs weighing less than 15 kg. A 1-2 milliliter volume of the preferred 65% by weight permethrin delivers 65-130 mg permethrin. On dogs larger than 15 kg, it has been found to be effective to apply 1 cc of 65% by weight permethrin composition between the shoulder blades in conjunction with another 1 ml at the tailhead. In a preferred embodiment, for every kilogram of the host body weight, about 33 or more milligrams of the composition should be applied.

The method for applying the preferred embodiment of the invention, its efficacy, as well as the absence of toxicity and irritation, is illustrated, by way of example only, by the following in-vivo experiments:

EXPERIMENT I

Animals

Twenty dogs were selected according to health and their ability to maintain parasite infestations and divided into four groups of five dogs each. The condition of each animal was checked daily.

On day 0, three groups of five dogs were treated with a dosage of a liquid formulation consisting of 65% by weight permethrin and 35% by weight 2-(2-methoxyethoxy)ethanol, and the other group of five dogs was left untreated. Treatments were applied to the skin by parting the hair in each treatment location. Treatment locations were between the shoulder blades and at the tailhead. Each treatment location received 1 milliliter of the formulation. Treatment groups are defined in Table 1 entitled Experimental Design.

TABLE 1

Experimental Design

| | |
|---|---|
| Group 1: | Five dogs of various weights - untreated |
| Group 2: | Five dogs less than 33 lbs receiving 1 treatment between the shoulder blades. |
| Group 3: | Five dogs less than 33 lbs receiving treatment between the shoulder blades and at the tailhead. |
| Group 4: | Five dogs over 33 lbs receiving treatment between the shoulder blades and at the tailhead. |

Infestations

One hundred unfed, adult fleas and 50 unfed, adult brown dog ticks were applied to each dog on the days specified in the following Activity Schedule. At each infestation the unfed, adult parasites were placed along the dorsal midline of each dog from its head to the base of its tail.

Parasite Counts

Counts were made of the live fleas and ticks remaining on each dog on the days specified in the following Activity Schedule given in Table 1. Tick records indicate the location, sex, and stage of engorgement of each live, attached tick.

The untreated dogs were counted first, and the examiners wore gloves during the examination. The examination table was washed and the examiners changed gloves following the examination of each treated group. Examinations were conducted according to the activity schedule shown in Table 2.

TABLE 2

Activity Schedule

| Day | Activity |
|---|---|
| −14 | Begin preconditioning dogs |
| −4 | Infest w/ticks |
| −1 | Infest w/ticks |
| 0 | Count fleas and ticks. Select dogs, weigh, assign to groups, and treat |
| 1 | Count fleas |
| 2 | Count fleas |
| 3 | Count fleas and ticks, remove ticks, reinfest w/ticks |
| 6 | Reinfest w/fleas |
| 7 | Count fleas and ticks, remove ticks |
| 10 | Reinfest w/ticks |
| 13 | Reinfest w/fleas |
| 14 | Count fleas and ticks, remove ticks |
| 19 | Reinfest w/ticks |
| 20 | Reinfest w/fleas |

TABLE 2-continued

Activity Schedule

| Day | Activity |
|---|---|
| 21 | Count fleas and ticks, remove ticks |
| 24 | Reinfest w/ticks |
| 27 | Reinfest w/fleas |
| 28 | Count fleas and ticks, remove ticks |
| 31 | Reinfest w/ticks |
| 34 | Reinfest w/fleas |
| 35 | Count fleas and ticks |

Evaluation
The following parameters were used for tabulating results:
(1) Visual counts of fleas (ticks) on host
(2) Percent control of fleas (ticks) on host =

$$100 \times \left( \frac{\text{Parasites on untreated dogs} - \text{parasites on treated dogs}}{\text{Parasites on untreated dogs}} \right)$$

RESULTS

Fleas

The three treatments with the preferred composition were performed similarly throughout the study with percent control ranging from 70 to 89 on Day 1, 87 to 100 on Day 2, 92 to 100 on Day 3, 99 to 100 on Day 7, 97 to 100 on Day 14, 99 to 100 on Day 21, 93 to 95 on Day 28 and 63 to 89 on Day 35. Group 3 (dogs weighing less than 33 pounds and treated with 1 cc. between the shoulder blades and 1 cc. at the tailhead) had noticeably higher control figures at Days 1 and 2 than Group 2 (dogs weighing less than 33 pounds and treated with 1 cc. between the shoulder blades only) and Group 4 (dogs weighing more than 33 pounds and treated with 1 cc. between the shoulder blades and 1 cc. at the tailhead). Group 3 reached 89 and 100 percent control at Days 1 and 2 respectively whereas Group 2 reached 75 and 90 percent control and Group 4 reached 70 and 92 percent control on Days 1 and 2. Also, from Day 3 through Day 28, Group 3 was slightly higher (one to eight percentage points) in percent control than Group 2 and Group 4.

A summary of flea counts and percent control of fleas is presented in Table 3.

TABLE 3

Groups defined in Text, p. 17.

| | TREATMENT | | | |
|---|---|---|---|---|
| TIME | Group 1 None | Group 2 less than 15 kg Shld. | Group 3 less than 15 kg Shld./Tail | Group 4 greater than 15 kg Shld./Tail |
| Day −1 Fleas | 209 | 274 | 270 | 209 |
| Day 1 | | | | |
| Fleas | 195 | 49 | 22 | 59 |
| % Control | | 75 | 89 | 70 |
| Day 2 | | | | |
| Fleas | 184 | 19 | 0 | 24 |
| % Control | | 90 | 100 | 87 |
| Day 3 | | | | |
| Fleas | 165 | 12 | 0 | 14 |
| % Control | | 93 | 100 | 92 |
| Day 7 | | | | |
| Fleas | 279 | 0 | 0 | 4 |
| % Control | | 100 | 100 | 99 |
| Day 14 | | | | |
| Fleas | 254 | 8 | 0 | 2 |
| % Control | | 97 | 100 | 99.2 |
| Day 21 | | | | |
| Fleas | 312 | 3 | 0 | 3 |

TABLE 3-continued

| | Groups defined in Text, p. 17. TREATMENT | | | |
|---|---|---|---|---|
| TIME | Group 1 None | Group 2 less than 15 kg Shld. | Group 3 less than 15 kg Shld./Tail | Group 4 greater than 15 kg Shld./Tail |
| % Control | | 99 | 100 | 99 |
| Day 28 | | | | |
| Fleas | 297 | 19 | 14 | 21 |
| % Control | | 94 | 95 | 93 |
| Day 35 | | | | |
| Fleas | 289 | 106 | 64 | 33 |
| % Control | | 63 | 78 | 89 |

[a. Shld. denotes that the treatment site was between the shoulder blades.]
[b. Shld./Tail denotes that treatments were at two sites, one between the shoulders and the other at the tailhead.]

Ticks

Control of attached ticks on Day 3 was 70 percent in Group 2, 59 percent in Group 3 and 49 percent in Group 4. Groups 2 and 3 were similar in control (96–100 percent control) of post-treatment tick infestation through Day 21. Group 4 stayed at 90 percent from Day 7 to 14 then increased to 98 percent control on Day 21. By Days 28 and 35 the tick control figures for all three groups were falling slightly to 88–96 percent on Day 28 and 84 to 92 percent on Day 35.

Tick counts and percent control are summarized in Table 4.

TABLE 4

| | Total ticks and percent control of Ticks: | | | |
|---|---|---|---|---|
| | Groups defined in Text, p. 18. TREATMENT | | | |
| TIME | Group 1 None | Group 2 less than 15 kg Shld. | Group 3 less than 15 kg Shld./Tail | Group 4 greater than 15 kg Shld./Tail |
| Day −1 Ticks | 131 | 99 | 98 | 114 |
| Day 3 | | | | |
| Ticks | 63 | 19 | 26 | 32 |
| % Control | | 70 | 59 | 49 |
| Day 7 | | | | |
| Ticks | 110 | 4 | 0 | 11 |
| % Control | | 96 | 100 | 90 |
| Day 14 | | | | |
| Ticks | 119 | 1 | 1 | 12 |
| % Control | | 99.1 | 99.1 | 90 |
| Day 21 | | | | |
| Ticks | 183 | 1 | 2 | 4 |
| % Control | | 99.5 | 99 | 98 |
| Day 28 | | | | |
| Ticks | 203 | 24 | 9 | 16 |
| % Control | | 88 | 96 | 92 |
| Day 35 | | | | |
| Ticks | 193 | 16 | 23 | 30 |
| % Control | | 92 | 88 | 84 |

[a. Shld. denotes treatment site was between the shoulder blades.]
[b. Shld./Tail denotes that treatments were at two sites, one between the shoulders and the other at the tailhead.]

Adverse Reaction

No adverse reactions occurred. An oily residue was evident in the hair surrounding the sites treated with the invented formulation, but no skin irritation, dermatitis, or hair loss occurred.

EXPERIMENT II

In this experiment, migration of the pyrethroid component of a composition made in accordance with this invention is observed. The pyrethroid component translocates from the region of application to cover virtually all of the animal body surface within 3 to 24 hours following application at a suitable concentration for effective ectoparasite control.

Experimental

Two healthy dogs of varying weight; dog "A" having a body weight below 15 kilograms (kg) and a dog "B" with a body weight above 15 kg were selected for the migration test. A composition made in accordance with this invention comprising about 65% of permethrin and about 35% of the carrier 2-(2-methoxyethoxy)ethanol was utilized. One cubic centimeter (cc) of the composition was applied as a spot between the shoulder blades of dog A. One cc of the composition was applied as a spot between the shoulder blades of dog B and another cc applied at the tail bone of dog B.

The body surface of each dog was hypothetically divided into 13 regions. At hours 0, 3, 6,12 and 24 following application, a hair sample was taken from each region of the dog. The hair samples were analyzed by qualitative techniques to determine the presence of permethrin.

Results

The permethrin was found in every region of both dogs within 24 hours of initial application. The smaller dog A was effectively covered within six hours of application and the larger dog B was effectively covered within 24 hours of application. The relatively high concentration of permethrin, 65%, enables the translocated permethrin to effectively control ectoparasites over relatively all of the animal's body.

EXPERIMENT III

Permethrin toxicity studies have been completed in numerous species, including rats, mice, rabbits, dogs, cats, cattle, poultry, swine and horses. This study documents the safety of the invention embodiment consisting of 65% permethrin and 35% 2(2-methoxyethoxy) ethanol on dogs.

Experimental Design

Five dogs were randomly assigned to each treatment group; two dogs served as untreated controls. All dogs were mixed breed, six months to one year of age and 15 to 25 pounds in weight.

Complete chemistry profiles were completed on each of 12 dogs prior to initiation of the study. Dogs were examined by a veterinarian and judged to be healthy prior to the treatment phase.

Treatment Regime

The two treatments consisted of 1 cc or 4 cc of 50% permethrin in 2-(2-methoxyethoxy)ethanol. Each dog was individually treated by administering the indicated amount of material (1 cc or 4 cc) to the shoulder blade area using a 1 cc eyedropper.

Dogs were observed for any signs of adverse reactions, including, but not limited to diarrhea, vomiting, salivation, excessive lacrimation, muscle fasciculations, hyperactivity, depression or anorexia. Dogs were noted as being normal if no signs were observable and the dog appeared similar to pretreatment observations and untreated dogs. Observations were noted immediately at the time of treatment, at two, four, six and eight hours after treatment and daily thereafter for four days. The treatment and observation process was repeated on days 7 through 11 and again on days 14–18, resulting in three treatments and three weeks of observations.

Results

No adverse reactions were noted in any dog at any time during the course of this study. All dogs exhibited normal behavior. Food and water consumption remained normal throughout the study.

Conclusion

No adverse reactions were noted after dogs were repeatedly treated with the preferred formulation (permethrin formulated as a ready-to-use spot-on topical applicant). Additionally, this formulation exhibits a wide margin of safety, with no acute toxicological reactions at 4× the effective dose. This study demonstrates that the most preferred formulation is safe for use on dogs even when applied at several times the recommended dose.

What is claimed is:

1. A parasiticidal composition for topical application to mammals comprising a pyrethroid in a carrier, wherein said carrier is an alkyl glycol ether and said pyrethroid is present in an amount greater than 50% and up to about 95% by weight of the total composition.

2. A composition according to claim 1, wherein said carrier is present in an amount ranging from 5% to about 50% by weight of the total composition.

3. A composition according to claim 2 wherein said alkyl glycol ether is selected from the group consisting of 2-(2-butoxyethoxy) ethanol and 2-(2-methoxyethoxy)ethanol.

4. A composition according to claim 1 wherein said pyrethroid is dissolved in said carrier.

5. A composition according to claim 1, wherein said pyrethroid is selected from the group consisting of permethrin, phenothrin, deltamethrin, cypermethrin, cyhalothrin, lambda cyhalothrin, flumethrin, cyfluthrin, cyphenothrin, sluvalinate fluvinate, tralomethrin, tralocythrin, and fenvalerate.

6. A composition according to claim 5, wherein said permethrin is selected from the group consisting of compositions of the formula:

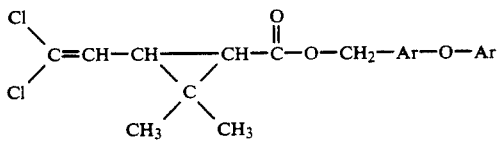

and stereo isomers thereof, Ar is a phenyl group.

7. A composition according to claim 1, wherein said pyrethroid is present in an amount of about 65% by weight of the total composition.

8. A composition according to claim 7, wherein said pyrethroid is a permethrin selected from the group consisting of compositions of the formula:

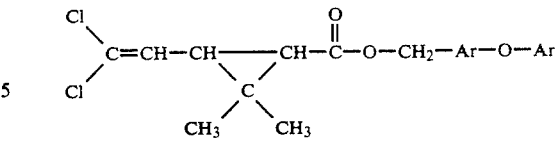

and stereo-isomers thereof, Ar is a phenyl group.

9. A composition according to claim 7, wherein said alkyl glycol ether is present in an amount of about 35% by weight of the total composition.

10. A composition according to claim 9, wherein said alkyl glycol ether is selected from the group consisting of: 2-(2-butoxyethoxy) ethanol, 2-(2-methoxyethoxy)ethanol and mixtures thereof.

11. A method of non-systemically controlling ectoparasite infestation on mammalian hosts comprising topically applying a parasiticidal composition to a localized external region on the mammal, said parasiticidal composition comprising a pyrethroid in a carrier said pyrethroid present in an amount greater than 50% and up to about 95% by weight of the total composition.

12. A method according to claim 11, wherein said method comprises applying said composition to one or more external localized region on the mammal, said composition comprising a pyrethroid in an alkyl glycol ether carrier.

13. A method according to claim 11 wherein said applying step comprises topically applying a parasiticidal composition on said mammal, said composition comprising a pyrethroid in a carrier wherein said carrier is selected from the group consisting of 2-(2-butoxyethoxy) ethanol and 2-(2-methoxyethoxy)ethanol.

14. A method according to claim 11, wherein said applying step comprises topically applying said parasiticidal composition to a localized external region on a mammal, said mammal selected from the group consisting of humans, dogs, cattle, giraffes and horses.

15. A method according to claim 14, wherein said applying step comprises topically applying said parasiticidal composition to a localized external region on a mammal, said mammal being a dog.

16. A method according to claim 11, wherein said applying step comprises topically applying 33.3 milligrams of said parasiticidal composition on the mammal per kilogram of said mammal's body weight.

17. A method according to claim 11 wherein said method of applying said composition to one or more localized external regions on the mammal is effective as a method for administering the pyrethroid component onto relatively all of the mammal's body surface.

18. A method according to claim 15 wherein said method of applying said composition to one or more localized external regions on the mammal comprises applying the composition to one or more regions each ranging from one to four cubic centimeters in size.

19. A method according to claim 17 wherein said method comprises applying said composition to one localized external region on the mammal.

20. A method according to claim 17 wherein said method comprises applying said composition to two localized external regions on the mammal.

21. A method according to claim 18 wherein said method of applying said composition to a localized external region on the mammal comprises applying said composition to a localized external region on the mammal as a spot.

22. A method according to claim 11, wherein said applying step comprises topically applying a parasiticidal composition on said mammal, said composition comprising a carrier in an amount ranging from 5% to about 50% by weight of the total composition.

23. A method according to claim 22, wherein said applying step comprises topically applying a parasiticidal composition on said mammal, said composition comprising a pyrethroid selected from the group consisting of permethrin, phenothrin, deltamethrin, cypermethrin, cyhalothrin, flumethrin, cyfluthrin, cyphenothrin, tralomethrin, tralocythrin and fenvalerate.

24. A method according to claim 23, wherein said applying step comprises topically applying a parasiticidal composition on said mammal, said composition comprising a permethrin selected from the group consisting of compositions of the formula:

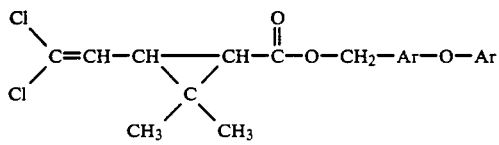

and stereo-isomers thereof, Ar is a phenyl group.

25. A method according of controlling ectoparasite infestation on non-human domestic animals comprising topically applying a parasiticidal composition to a localized external region on the mammal, said parasiticidal composition comprising a pyrethroid in a carrier wherein said carrier is an alkyl glycol ether and said pyrethroid is present in an amount of about 65% by weight of the total composition.

26. A method according to claim 25, wherein said applying step comprises applying a parasiticidal composition on said mammal, said composition comprising a pyrethroid in a carrier wherein said carrier is present in an amount of about 35% by weight of the total composition.

27. A method according to claim 26, wherein said applying step comprises topically applying a parasiticidal composition on said mammal, said composition comprising a pyrethroid in a carrier wherein the carrier is selected from the group consisting of 2-(2-butoxyethoxy) ethanol, 2-(2-methoxyethoxy)ethanol and mixtures thereof.

28. A method according to claim 27, wherein said applying step comprises topically applying one milliliter of said parasiticidal composition on said mammal, wherein said mammal weighs less than 15 kilograms.

* * * * *

UNITED STATES PATENT AND TRADEMARK OFFICE
CERTIFICATE OF CORRECTION

PATENT NO. : 5,236,954

DATED : August 17, 1993

INVENTOR(S) : Julie G. Gladney, David S. Seymour, Jack I. Shugart, Robert G. Pennington It is certified that error appears in the above-identified patent and that said Letters Patent is hereby corrected as shown below:

Column 4, line 55, delete the word "" of" and substitute -- on --

Col. 5, line 5, delete the word "Diproylene" and substitute --Dipropylene--

Column 5, line 21, delete the word "aglinates" and substitute -- alginates --

Column 5, line 62, delete the word "additional" should read --traditional--

Column 5, line 67, delete the word "take" and substitute -- tank --

Column 6, line 26, delete the word "ma" and substitute -- may --

Column 6, line 42, delete the word "u" and substitute -- up --

Column 7, line 55, table 2, reads "-1 Infest w/ticks" and should read -- -1 Infest w/fleas --

Column 9, line 23, following the word "percent" insert the word --control--

Column 14, line 1, delete the word "according"

UNITED STATES PATENT AND TRADEMARK OFFICE
CERTIFICATE OF CORRECTION

PATENT NO. : 5,236,954

DATED : August 17, 1993

INVENTOR(S) : Julie G. Gladney, David S. Seymour, Jack I. Shugart, Robert G. Pennington It is certified that error appears in the above-indentified patent and that said Letters Patent is hereby corrected as shown below:

Column 14, line 2, delete the word "animals" and substitute -- mammals --

Signed and Sealed this

Twenty-fourth Day of May, 1994

Attest:

BRUCE LEHMAN

Attesting Officer

Commissioner of Patents and Trademarks